(12) United States Patent
Nagai et al.

(10) Patent No.: US 12,367,660 B2
(45) Date of Patent: Jul. 22, 2025

(54) LEARNING SYSTEM FOR CREATING TRAINED MODEL THAT PREDICTS COMPLETE RECOVERY PERIOD OF AFFECTED PART, CONTROL METHOD FOR SAME, AND STORAGE MEDIUM

(71) Applicant: CANON KABUSHIKI KAISHA, Tokyo (JP)

(72) Inventors: Keita Nagai, Tokyo (JP); Kazuomi Toguchi, Kanagawa (JP); Honami Watanabe, Tochigi (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 408 days.

(21) Appl. No.: 17/979,828

(22) Filed: Nov. 3, 2022

(65) Prior Publication Data
US 2023/0169756 A1    Jun. 1, 2023

(30) Foreign Application Priority Data

Nov. 30, 2021   (JP) .................. 2021-194558

(51) Int. Cl.
| | | |
|---|---|---|
| *G06V 10/774* | (2022.01) | |
| *A61B 5/00* | (2006.01) | |
| *G06T 7/00* | (2017.01) | |
| *G16H 50/50* | (2018.01) | |

(52) U.S. Cl.
CPC .......... *G06V 10/774* (2022.01); *A61B 5/0077* (2013.01); *A61B 5/7267* (2013.01); *G06T 7/0016* (2013.01); *G16H 50/50* (2018.01); *G06T 2207/20081* (2013.01); *G06T 2207/20084* (2013.01); *G06V 2201/03* (2022.01)

(58) Field of Classification Search
CPC .. G06V 10/774; G06V 2201/03; G06V 10/82; A61B 5/0077; A61B 5/7267; A61B 5/445; G06T 7/0016; G06T 2207/20081; G06T 2207/20084; G16H 50/50; G16H 30/20; G16H 40/20; G16H 50/70; G16H 30/40; G16H 50/20
See application file for complete search history.

(56) References Cited

FOREIGN PATENT DOCUMENTS

| CN | 112992358 A | * | 6/2021 |
| CN | 113017570 A | * | 6/2021 |
| JP | 2020-095600 A | | 6/2020 |

* cited by examiner

*Primary Examiner* — Xin Jia
(74) *Attorney, Agent, or Firm* — Carter, DeLuca & Farrell LLP

(57) ABSTRACT

A learning system which is capable of easily collecting data of affected parts having completely recovered, as training data. When it is determined that an affected part has completely recovered based on affected-part image data generated by shooting the affected part, image data accompanied with the same affected part ID as that of the affected-part image data is identified from among image data set stored in a storage device of the learning system. The actual number of days to a complete recovery of the affected part is calculated from shooting dates of the identified image data and the affected-part image data, and is added to the affected-part image data. The affected-part image data accompanied with the actual number of days to the complete recovery is used as training data to create a trained model that predicts the number of days to a complete recovery of the affected part.

7 Claims, 17 Drawing Sheets

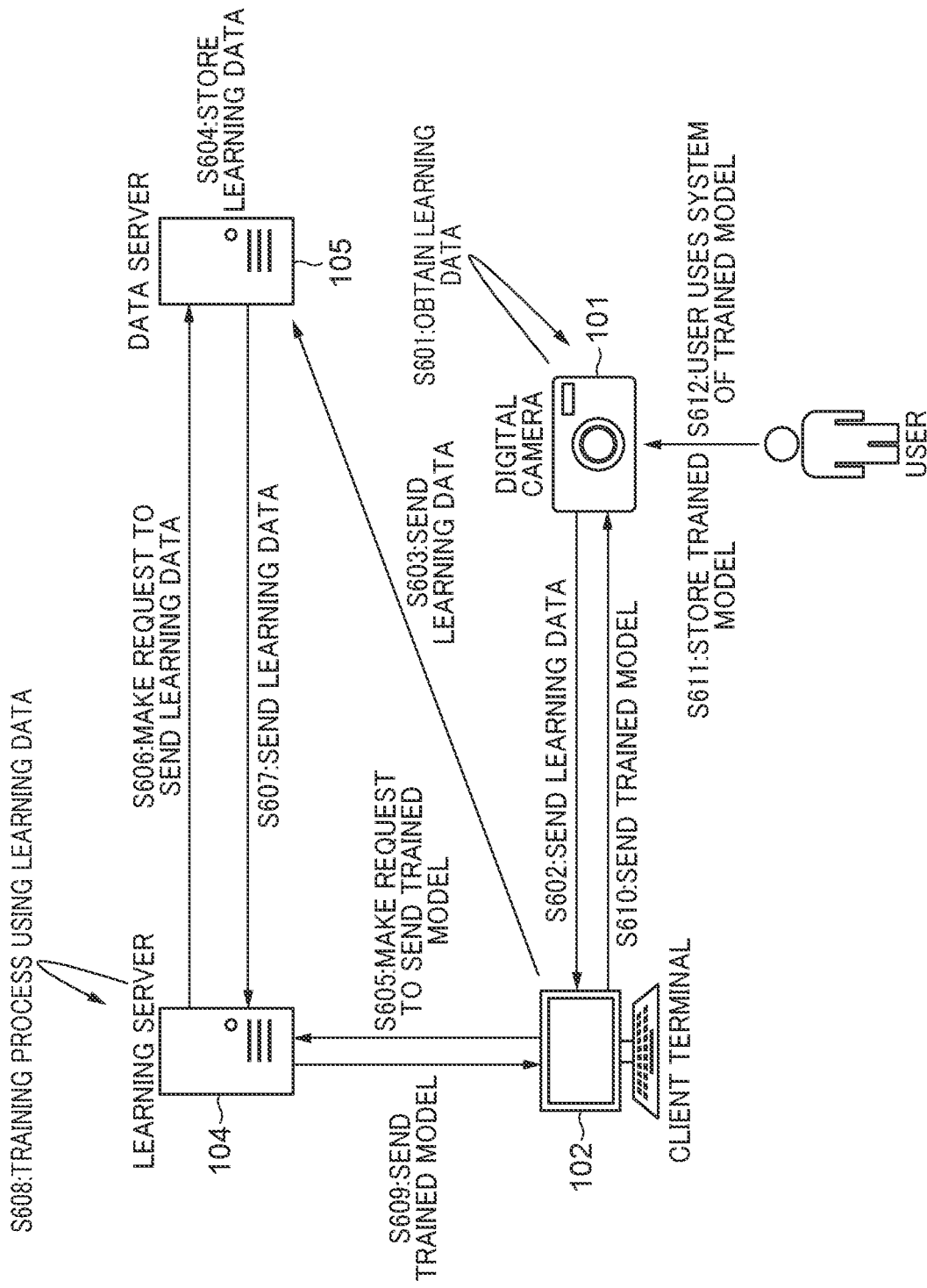

FIG. 8A

| IMAGE | |
|---|---|
| METADATA1 | |
| METADATA2 | |
| METADATA3 | |
| METADATA4 | |

FIG. 8B

| IMAGE | |
|---|---|
| METADATA1 | |
| METADATA2 | AFFECTED PART ID: xxxxxx |
| METADATA3 | SHOOTING DATE: 2021/1/1 |
| METADATA4 | |

FIG. 8C

| METADATA1 | IMAGE |
|---|---|
| METADATA2 | AFFECTED PART ID: xxxxxx |
| METADATA3 | SHOOTING DATE: 2021/1/1 |
| METADATA4 | COMPLETE RECOVERY FLAG: 1 |

FIG. 8D

| METADATA1 | IMAGE |
|---|---|
| METADATA2 | AFFECTED PART ID: xxxxxx |
| METADATA3 | SHOOTING DATE: 2021/1/1 |
| METADATA4 | COMPLETE RECOVERY FLAG: 1 |
| | ACTUAL NUMBER OF DAYS TO COMPLETE RECOVERY: 10 DAYS |

FIG. 10A

| IMAGE | | |
|---|---|---|
| METADATA1 | AFFECTED PART ID: xxxxx | |
| METADATA2 | SHOOTING DATE: 2021/1/1 | |
| METADATA3 | | |
| METADATA4 | | |
| METADATA5 | | |
| METADATA6 | | |
| METADATA7 | | |

FIG. 10B

| IMAGE | | |
|---|---|---|
| METADATA1 | AFFECTED PART ID: xxxxx | |
| METADATA2 | SHOOTING DATE: 2021/1/1 | |
| METADATA3 | COMPLETE RECOVERY FLAG: 1 | |
| METADATA4 | PREDICTED NUMBER OF DAYS TO COMPLETE RECOVERY: 12 DAYS | |
| METADATA5 | | |
| METADATA6 | | |
| METADATA7 | | |

*FIG. 10C*

| IMAGE | |
|---|---|
| METADATA1 | AFFECTED PART ID: xxxxxx |
| METADATA2 | SHOOTING DATE: 2021/1/1 |
| METADATA3 | COMPLETE RECOVERY FLAG: 1 |
| METADATA4 | PREDICTED NUMBER OF DAYS TO COMPLETE RECOVERY: 12 DAYS |
| METADATA5 | ACTUCAL NUMBER OF DAYS TO COMPLETE RECOVERY: 10 DAYS |
| METADATA6 | COMPARISON RESULT: 2 DAYS |
| METADATA7 | RETRAINING FLAG: 1 |

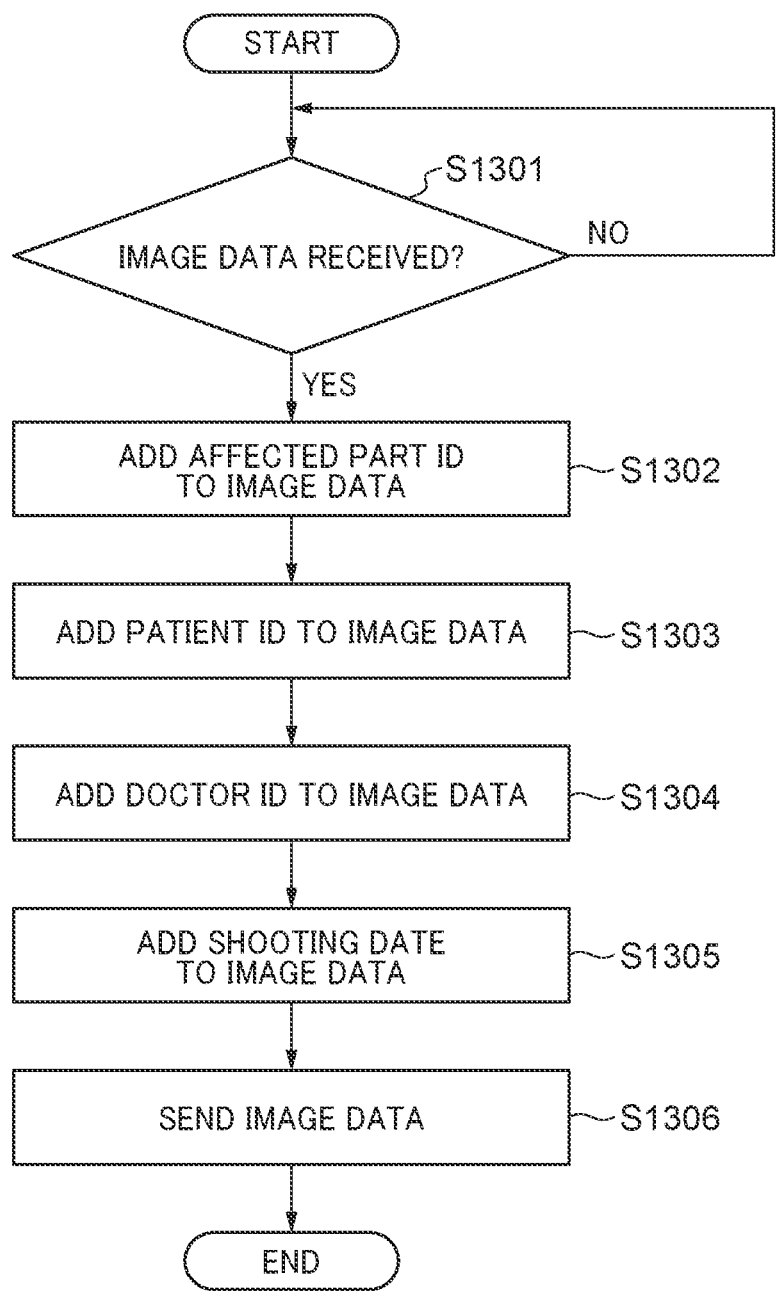

FIG. 14A

| IMAGE | | |
|---|---|---|
| METADATA1 | AFFECTED PART ID: xxxxx | |
| METADATA2 | PATIENT ID: yyyyy | |
| METADATA3 | DOCTOR ID: zzzzz | |
| METADATA4 | SHOOTING DATE: 2021/1/1 | |
| METADATA5 | | |
| METADATA6 | | |

FIG. 14B

| IMAGE | | |
|---|---|---|
| METADATA1 | AFFECTED PART ID: xxxxx | |
| METADATA2 | PATIENT ID: yyyyy | |
| METADATA3 | DOCTOR ID: zzzzz | |
| METADATA4 | SHOOTING DATE: 2021/1/1 | |
| METADATA5 | COMPLETE RECOVERY FLAG: 1 | |
| METADATA6 | ACTUCAL NUMBER OF DAYS TO COMPLETE RECOVERY: 10 DAYS | |

LEARNING SYSTEM FOR CREATING TRAINED MODEL THAT PREDICTS COMPLETE RECOVERY PERIOD OF AFFECTED PART, CONTROL METHOD FOR SAME, AND STORAGE MEDIUM

BACKGROUND OF THE INVENTION

Field of the Invention

The present invention relates to a learning system, a control method for the learning system, and a storage medium.

Description of the Related Art

AI (Artificial Intelligence) is used in clinical environments, and for example, AI is used in diagnosis on image data of an affected part of a patient obtained by shooting the affected part (see, for example, Japanese Laid-Open Patent Publication No. 2020-95600). Moreover, in clinical environments, to efficiently schedule patient visits, using a learning model (or a machine learning model) that predicts the number of days to a complete recovery of an affected part of a patient from image data of the affected part is being considered.

To train the learning model, training data, which is data on various affected parts having actually recovered completely, needs to be prepared and input to the learning model. Namely, a large amount of data needs to be collected as training data, and this requires a lot of time and effort.

SUMMARY OF THE INVENTION

The present invention provides a learning system, which is capable of easily collecting data of affected parts having completely recovered to be used as training data (which is also referred to as supervising data), a control method for the learning system, and a storage medium.

According to an aspect of the invention, a learning system includes a storage device; and at least one processor and/or at least one circuit configured to perform the following operations. Based on affected-part image data generated by shooting an affected part, the at least one processor and/or at least one circuit determines whether or not the affected part has completely recovered. In a case where it is determined that the affected part has completely recovered, the at least one processor and/or at least one circuit identifies image data accompanied with a same affected part ID as an affected part ID of the affected-part image data from among a plurality of image data stored in advance in the storage device, and calculates the actual number of days to a complete recovery of the affected part based on a shooting date of the identified image data and a shooting date of the affected-part image data. The at least one processor and/or at least one circuit adds the actual number of days to the complete recovery to the affected-part image data; and uses, as training data, the affected-part image data accompanied with the actual number of days to the complete recovery to create a trained model that predicts the number of days to a complete recovery of the affected part.

According to the present invention, in the learning system that predicts the number of days required for a complete recovery of an affected part, data of affected parts having actually recovered completely, which is to be used as training data, can be easily collected.

Further features of the present invention will become apparent from the following description of exemplary embodiments with reference to the attached drawings.

BRIEF DESCRIPTION OF THE DRAWINGS

FIG. 6 is a view illustrating the flow of data in the learning system in FIG. 1.

FIGS. 8A to 8D are views illustrating examples of a structure of image data for use in the first collection control process.

FIGS. 10A to 10C are views illustrating examples of the structure of image data for use in a second collection control process.

FIG. 13 is a flowchart illustrating an example of a process that is carried out by the client terminal in a third collection control process.

FIGS. 14A and 14B are views illustrating examples of the structure of image data for use in the third collection control process.

DESCRIPTION OF THE EMBODIMENTS

Embodiments of the present invention will now be described in detail with reference to the drawings. Arrangements in embodiments described below, however, are just examples, and the scope of the prevent invention is not limited by the arrangements in the embodiments described below.

Figure 1:
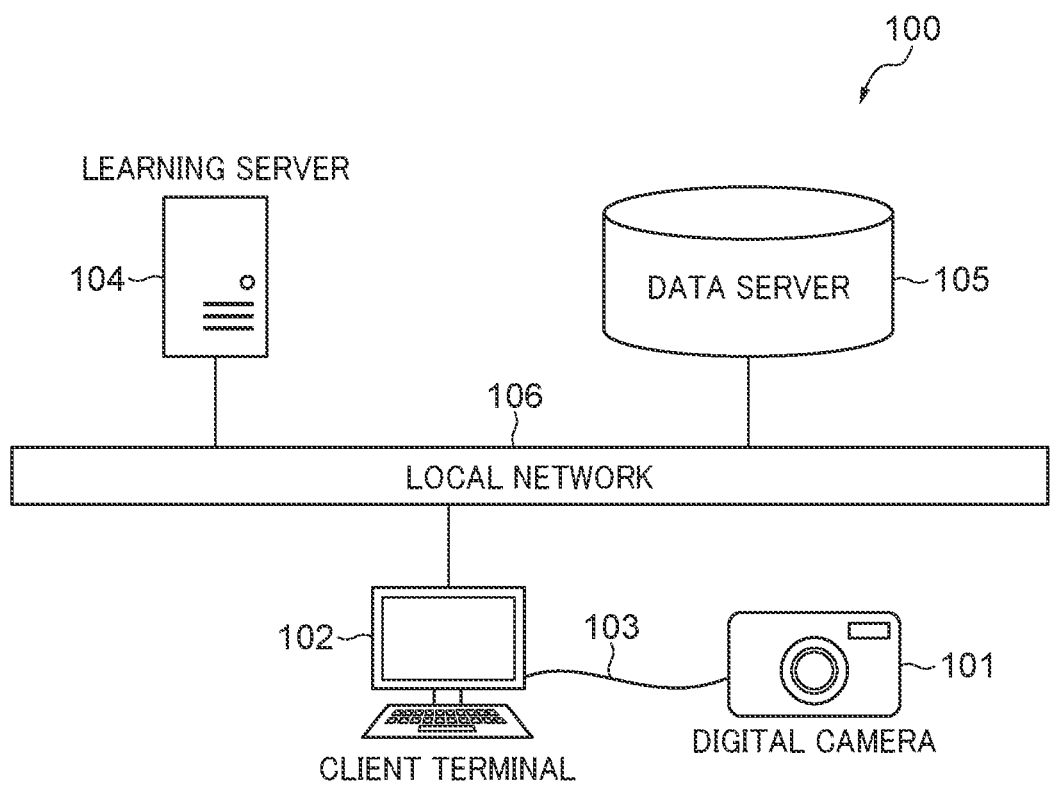
FIG. 1 is a view illustrating an example of a learning system according to an embodiment of the present invention.

FIG. 1 is a view illustrating an example of a learning system (or a machine learning system) 100 according to the present embodiment. Referring to FIG. 1, the learning system 100 includes a digital camera 101, a client terminal 102, a learning server 104, and a data server 105. The digital camera 101 is an electronic apparatus that is used by a user. Although the following description is given on the assumption that the digital camera 101 is an example of an electronic apparatus, the present embodiment is applicable to any arbitrary electronic apparatus. For example, the electronic apparatus may be a mobile terminal like a smartphone or tablet terminal or may be any arbitrary digital camera. The digital camera 101 is connected to the client terminal 102 such that they can communicate with each other via a communication unit 103. Communication via the communication unit 103 may be either wired communication like USB communication or wireless communication like Wi-Fi or Bluetooth communication.

The learning server 104 is a learning apparatus capable of training a learning model in machine learning. In the following description, it is assumed that the learning server 104 employs, but is not limited to, a deep learning algorithm for the machine learning. The learning server 104 may perform machine learning using any arbitrary machine learning algorithm such as a decision tree or a support vector machine.

The learning server 104 is connected to the data server 105 via a local network 106 such that they can communicate with each other. The client terminal 102 is capable of carrying out communications with the learning server 104 using wired communication or wireless communication via the local network 106. The learning server 104 is, for example, a cloud server or an edge computer.

Figure 2:
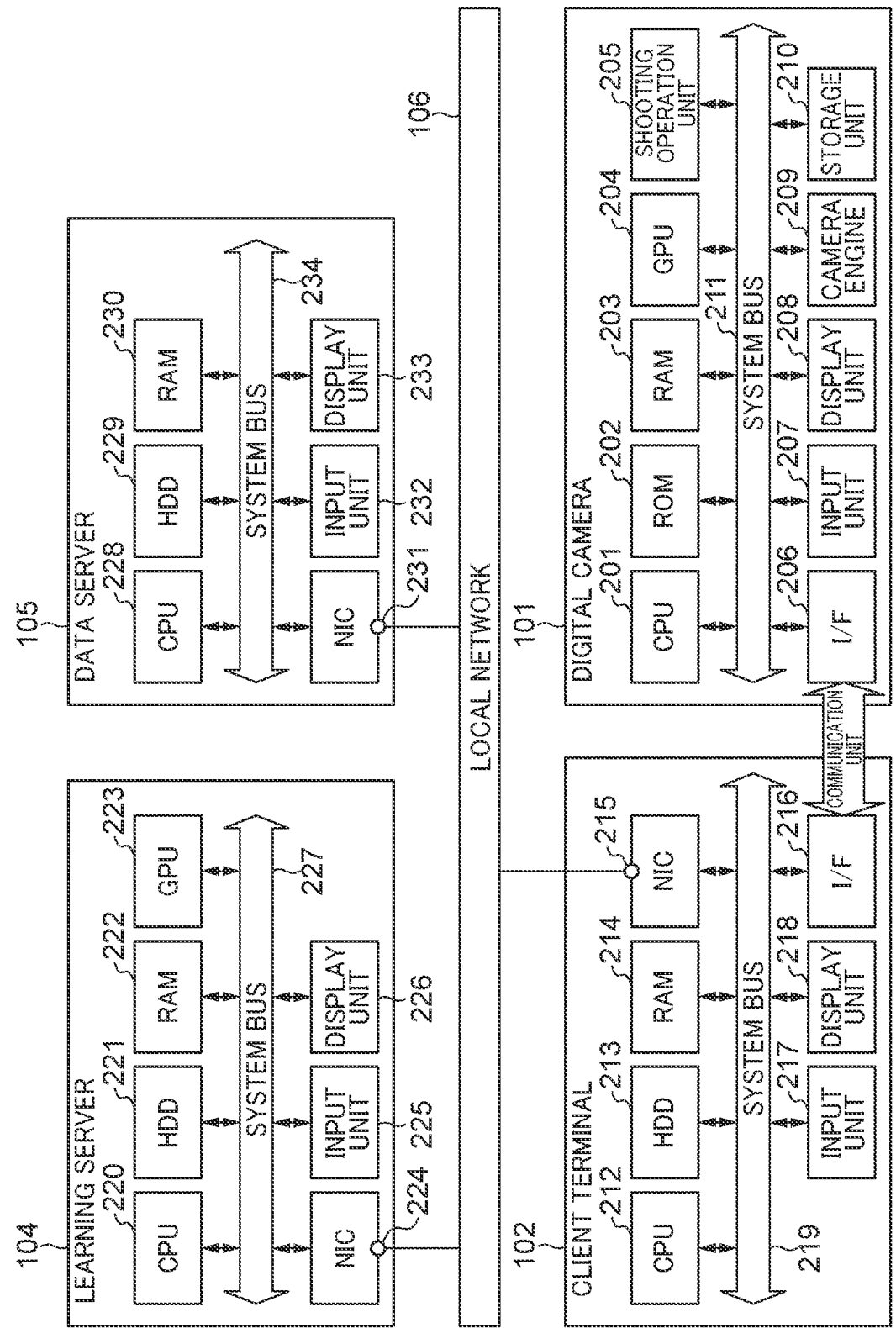
FIG. 2 is a view illustrating hardware arrangements of respective apparatuses in FIG. 1.

FIG. 2 is a view illustrating hardware arrangements of the respective apparatuses in FIG. 1. First, a description will be given of the digital camera 101. A CPU 201 is configured to control the overall operation of the digital camera 101. The CPU 201 also serves as a controller that controls power supply. A ROM 202 stores programs and data for operation of the CPU 201. A RAM 203 is a memory into which programs and operational data read from the ROM 202 by the CPU 201 are temporarily loaded. Processing in the digital camera 101 according to the present embodiment is implemented by the CPU 201 executing programs loaded into the RAM 203. A GPU 204 is an integrated circuit specialized for arithmetic processing so as to perform arithmetic operations for image processing and matrix operations at high speed and process a large amount of data in parallel. The GPU 204 is capable of efficiently performing arithmetic operations by processing a large amount of data in parallel. Examples of the arithmetic operations performed by the GPU 204 include a multiply-accumulate operation.

The GPU 204 is suitably used to carry out a prediction process using a trained deep-learning model. Accordingly, in the present embodiment, it is assumed that the GPU 204 carries out a prediction process using a trained model, which is a learning model trained by deep learning. The prediction process may be carried out by the CPU 201 or may be carried out by the CPU 201 and the GPU 204 working in cooperation with each other.

A shooting operation unit 205 is configured to receive a shooting operation from a user. When the CPU 201 detects that a user has performed a shooting operation on the shooting operation unit 205, the digital camera 101 is caused to take a shot. An I/F 206 is an interface for the digital camera 101 and the client terminal 102 to send and receive data to and from each other via the communication unit 103. An input unit 207 includes an image sensor and a motion sensor. The image sensor is a sensor used for the digital camera 101 to take shots. The motion sensor is configured to detect motions for correcting camera shake. The input unit 207 also has a function of receiving instructions from a user. For example, the input unit 207 is configured to receive an instruction for the digital camera 101 to take a shot, an instruction issued using a switch for designating a camera operation mode, and so forth.

A display unit 208 is capable of displaying an image being shot by the image sensor of the input unit 207, an image shot by the image sensor of the input unit 207, an operating state, and other types of information. A camera engine 209 is configured to process images obtained by the image sensor of the input unit 207. The camera engine 209 is also configured to perform image processing for displaying images, which are stored in a storage unit 210, on the display unit 208. The storage unit 210 stores image data of still images and video shot by the digital camera 101. A system bus 211 connects the blocks constituting the digital camera 101 with one another.

A description will now be given of the client terminal 102. A CPU 212 is configured to control the overall operation of the client terminal 102. An HDD 213 stores programs and data for operation of the CPU 212. A RAM 214 is a memory into which programs and operational data read from the HDD 213 by the CPU 212 are temporarily loaded. Processing in the client terminal 102 according to the present embodiment is implemented by the CPU 212 executing programs loaded into the RAM 214. A NIC 215 is an interface card that communicates with the learning server 104 and the data server 105 via the local network 106.

An I/F 216 is an interface for the client terminal 102 and the digital camera 101 to send and receive data to and from each other via the communication unit 103. An input unit 217 includes a keyboard, a mouse, and/or other devices that allow a user to operate the client terminal 102. A display unit 218 is configured to display information input to the client terminal 102 and other kinds of information. A system bus 219 connects the blocks constituting the client terminal 102 with one another.

A description will now be given of the learning server 104. A CPU 220 is configured to control the overall operation of the learning server 104. An HDD 221 stores programs and data for operation of the CPU 220. For example, a learning program including a learning model may be stored in the HDD 221. A RAM 222 is a memory into which programs and operational data read from the HDD 221 by the CPU 220 are temporarily loaded. Processing in the learning server 104 according to the present embodiment is implemented by the CPU 220 executing programs loaded into the RAM 222. As with the GPU 204, a GPU 223 is an integrated circuit capable of efficiently processing a large amount of data in parallel. Thus, the GPU 223 is a circuit suitable for a training process. It should be noted that the training process in the learning server 104 is carried out by the GPU 223. The training process may be carried out by the CPU 220 or may be carried out by the CPU 220 and the GPU 223 working in cooperation with each other. In the present embodiment, the training process carried out by the learning server 104 is implemented by executing a learning program including the learning model.

A NIC 224 is an interface card that communicates with the client terminal 102 and the data server 105 via the local network 106. An input unit 225 includes a keyboard, a mouse, and/or other devices that allow a user to operate the learning server 104. A display unit 226 is configured to display information input to the learning server 104 and other kinds of information. The display unit 226 is, for example, a display. A system bus 227 connects the blocks constituting the learning server 104 with one another.

A description will now be given of the data server 105. A CPU 228 is configured to control the overall operation of the data server 105. An HDD 229 stores programs and data for operation of the CPU 228. A RAM 230 is a memory into which programs and operational data read from the HDD 229 by the CPU 228 are temporarily loaded. Processing in the data server 105 according to the present embodiment is implemented by the CPU 228 executing programs loaded into the RAM 230. A NIC 231 is an interface card that communicates with the client terminal 102 and the learning server 104 via the local network 106. An input unit 232 includes a keyboard, a mouse, and/or other devices that allow a user to operate the data server 105. A display unit 233 is configured to display information input to the data server 105 and other kinds of information. The display unit 233 is, for example, a display. A system bus 234 connects the blocks constituting the data server 105 with one another.

Figure 3:
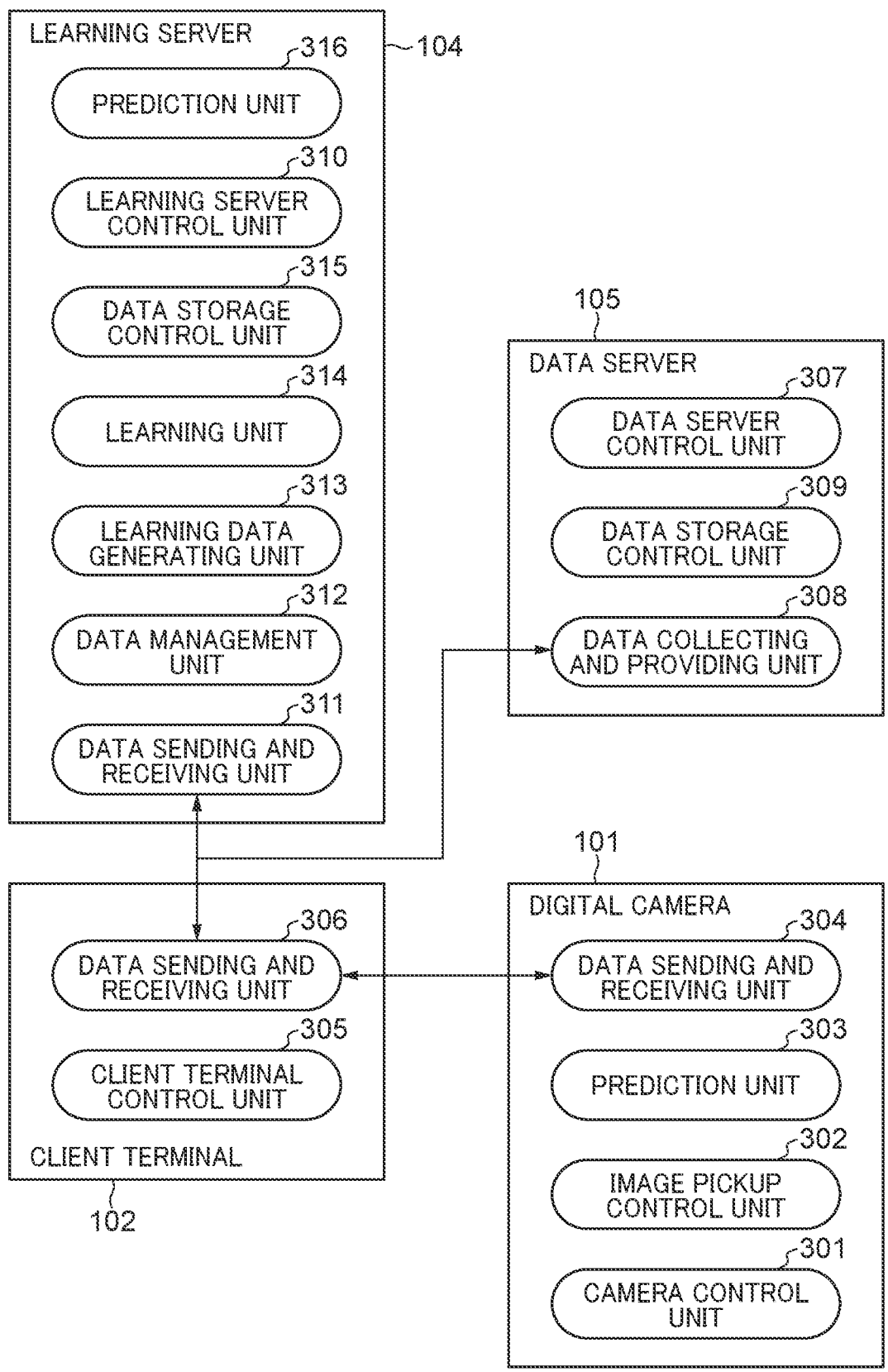
FIG. 3 is a view illustrating software functional blocks in the apparatuses in FIG. 2.

A description will now be given of software functions of the apparatuses in FIG. 2. FIG. 3 is a view illustrating blocks of the software functions of the apparatuses in FIG. 2. A camera control unit 301 of the digital camera 101 is a controller for controlling the entire digital camera 101. The camera control unit 301 is implemented by the CPU 201 executing programs loaded into the RAM 203. In response to a user operation received by the shooting operation unit 205 or the input unit 207, the camera control unit 301 is configured to cause the camera engine 209 to process an input from the image sensor. Also, in response to a user operation received by the input unit 207, the camera control unit 301 is configured to control the display unit 208 to display image data stored in the storage unit 210.

An image pickup control unit 302 is configured to obtain an image with the image sensor in response to a release instruction received by the shooting operation unit 205. For example, the image pickup control unit 302 is configured to obtain image data generated by shooting an affected part of a patient and outputs the image data to a prediction unit 303. The prediction unit 303 is configured to input the image data obtained from the image pickup control unit 302 to a trained model and carries out a prediction process. The prediction unit 303 is implemented by the GPU 204. A data sending and receiving unit 304 is configured to send image data obtained from the image pickup control unit 302 to the client terminal 102 that communicates with the data server 105. The data server 105 is configured to manage learning data for use in machine learning by the learning server 104. The data sending and receiving unit 304 is also configured to receive, from the client terminal 102 via the I/F 206, a trained model trained by the machine learning by the learning server 104.

A client terminal control unit 305 of the client terminal 102 is implemented by the CPU 212 executing programs loaded into the RAM 214. The client terminal control unit 305 is configured to control the entire client terminal 102. For example, assume that a user has issued an instruction to request transmission of learning data to the input unit 217 while viewing the display unit 218. In this case, according to the instruction issued to the input unit 217, the client terminal control unit 305 issues an instruction to obtain the learning data from the digital camera 101 and send the obtained learning data to the data server 105. Assume that a user has issued an instruction to request transmission of a trained model to the input unit 217 while viewing the display unit 218. In this case, according to the instruction issued to the input unit 217, the client terminal control unit 305 issues an instruction to obtain the trained model from learning server 104 and send the obtained trained model to the digital camera 101.

A data sending and receiving unit 306 is configured to receive the learning data, which has been sent from the digital camera 101, via the I/F 216 and send the learning data to the data server 105 via the NIC 215. The data sending and receiving unit 306 is also configured to receive a trained model, which has been created as a result of learning by the learning server 104, via the NIC 215 and send the trained model to the digital camera 101 via the I/F 216.

A data server control unit 307 of the data server 105 is implemented by the CPU 228 executing programs loaded into the RAM 230. The data server control unit 307 is configured to control the entire data server 105. Upon receiving learning data from the client terminal 102, the data server control unit 307 is configured to pass the learning data to a data storage control unit 309 and cause the data storage control unit 309 to store the learning data in the HDD 229. Also, upon receiving a request to send learning data from the learning server 104, the data server control unit 307 is configured to send the learning data to the learning server 104. A data collecting and providing unit 308 is configured to collect data by causing the NIC 231 to receive learning data sent from the client terminal 102. The data storage control unit 309 is configured to store the learning data, which is received by the NIC 231, in the HDD 229. The data storage control unit 309 is also configured to read learning data for use in machining learning by the learning server 104 from the HDD 229 and pass the read learning data to the NIC 231. The data collecting and providing unit 308 is configured to send learning data for use in machining learning by the learning server 104 to the learning server 104 via the NIC 231.

A learning server control unit 310 of the learning server 104 is implemented by the CPU 220 executing programs loaded into the RAM 222. The learning server control unit 310 is configured to control the entire learning server 104. For example, assume that the user has issued an instruction to carry out a training process while viewing the display unit 226. According to the instruction to carry out the learning training process, the learning server control unit 310 is configured to obtain learning data from the data server 105. The learning server control unit 310 is configured to cause a learning unit 314 to perform machine learning using the obtained learning data. The learning server control unit 310 is configured to send a trained model, which is created as a result of machine learning by the learning unit 314, to the client terminal 102. A data sending and receiving unit 311 is configured to receive the learning data, which is sent from the data server 105, via the NIC 224. The data sending and receiving unit 311 is also configured to send the trained model to the client terminal 102 via the NIC 224.

A data management unit 312 is configured to determine whether to use the learning data received by the data sending and receiving unit 311 and determine whether to send the trained model from the data sending and receiving unit 311. A learning data generating unit 313 is configured to carry out a process in which it loads data received as the learning data by the data management unit 312 into the RAM 222 and processes the data into data suitable to training a learning model. The data generated by the learning data generating unit 313 is stored in the RAM 222 or the HDD 221.

The learning unit 314 is configured to perform machine learning to train a learning model using the learning data stored in the RAM 222 or the HDD 221. Functions of the learning unit 314 are implemented by the GPU 223. A data storage control unit 315 stores a trained model, which is created as a result of machine learning performed by the learning unit 314, in the HDD 221. A prediction unit 316 is configured to input image data obtained from the client terminal 102 as unknown or new image data to the trained model and carries out a prediction process. The prediction unit 316 is implemented by the GPU 223.

Figure 4:
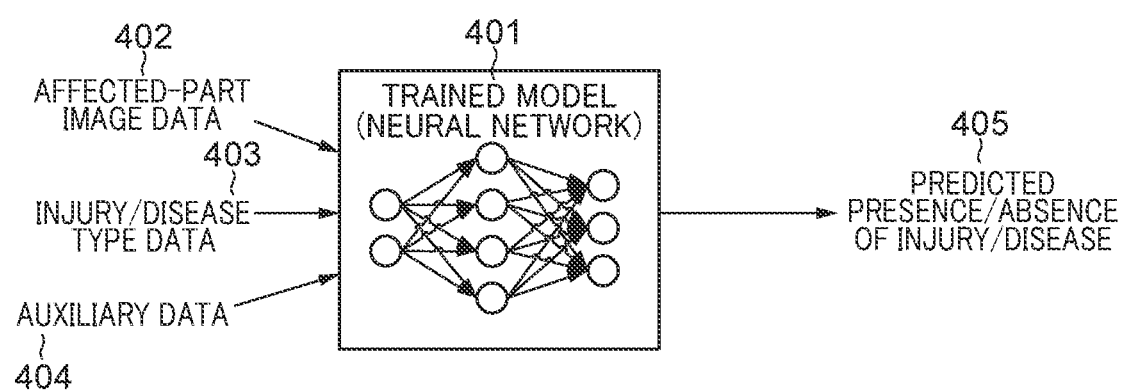
FIG. 4 is a view illustrating data input to and output from a model that predicts the presence/absence of an affected part and is to be used by a prediction unit in FIG. 3.

FIG. 4 is a view illustrating data input to and output from an affected-part presence/absence prediction model 401, which is a trained model to be used by the prediction unit 316 in FIG. 3. In the description of the present embodiment, it is assumed that the affected-part presence/absence prediction model 401 is based on, but is not limited to, neural networks. Affected-part image data 402, injury/disease type data 403, and auxiliary data 404 are input as unknown data to the affected-part presence/absence prediction model 401. The affected-part image data 402 is image data generated by the image pickup control unit 302 of the digital camera 101 shooting an affected part. The injury/disease type data 403 is data indicating a type of injury or disease of the affected part. It should be noted that the injury/disease type data 403 may automatically reflect information read from an electronic medical record or may be determined based on the affected-part image data 402 by the affected-part presence/absence prediction model 401. In the case where the injury/disease type data 403 is determined based on the affected-part image data 402 by the affected-part presence/absence prediction model 401, it is not necessary to prepare inputs other than affected-part image data 402 to determine the injury/disease type data 403. The auxiliary data 404 is data useful in determining the presence or absence of injury or disease, like skin color data on a patent. The affected-part presence/absence prediction model 401 receives the affected-part image data 402, the injury/disease type data 403, and the auxiliary data 404 to carry out the prediction process and outputs a predicted presence/absence of injury/disease 405 as a prediction result. The predicted presence/absence of injury/disease 405 is a prediction result indicating whether the affected part is present or absent in the affected-part image data 402.

Figure 5:
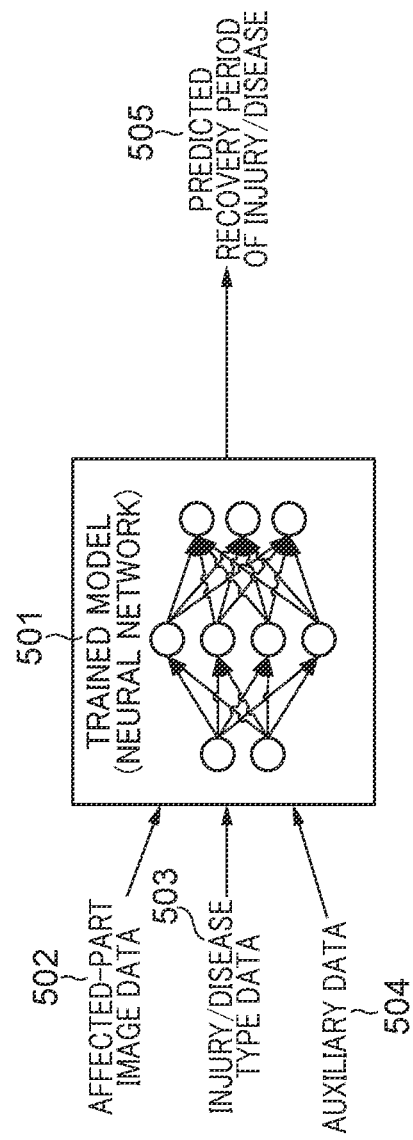
FIG. 5 is a view illustrating data input to and output from a model that predicts the number of days to a complete recovery.

A description will now be given of a prediction process carried out by a complete-recovery period prediction model 501, which is a trained model created as a result of machine learning by the learning unit 314 in FIG. 3. The complete-recovery period prediction model 501 predicts the days to a complete recovery of an affected part. FIG. 5 is a view illustrating data input to and output from the complete-recovery period prediction model 501. In the present embodiment, it is assumed that the complete-recovery period prediction model 501 is based on, but is not limited to, neural networks as with the affected-part presence/absence prediction model 401.

Affected-part image data 502, injury/disease type data 503, and auxiliary data 504 are input as unknown data to the complete-recovery period prediction model 501. The affected-part image data 502 has the same data structure as that of the affected-part image data 402. The injury/disease type data 503 has the same data structure as that of the injury/disease type data 403. The auxiliary data 504 is auxiliary data for predicting the number of days to a complete recovery of an affected part that appears in the injury/disease type data 503, and examples of the auxiliary data 504 include medication information and intake nutrition information. The complete-recovery period prediction model 501 receives the affected-part image data 502, the injury/disease type data 503, and the auxiliary data 504 to carry out the prediction process and outputs a predicted recovery period of injury/disease 505 as a prediction result. The predicted recovery period of injury/disease 505 is a prediction result indicating the number of days to a complete recovery of an affected part that appears in the affected-part image data 502.

A description will now be given of the flow of data. FIG. 6 is a view illustrating the flow of data in the learning system 100. First, the CPU 201 of the digital camera 101 obtains learning data from the image pickup control unit 302 (step S601). The learning data is affected-part image data generated by the image pickup control unit 302 shooting an affected part. It should be noted that at this time, data indicating the type of injury/disease of an affected part, medication information, intake nutrition information, and so forth obtained from an electronic medical record may be recorded as metadata for the learning data. Second, the CPU 201 sends the obtained learning data to the client terminal 102 (step S602). Third, the CPU 212 of the client terminal 102 sends the received learning data to the data server 105 (step S603).

Fourth, the CPU 228 of the data server 105 stores the received learning data in the HDD 229 (step S604). Fifth, the CPU 212 of the client terminal 102 outputs a request to send a trained model, which will be sent to the digital camera 101, to the learning server 104 (step S605). Sixth, upon receiving the request to send the trained model, the CPU 220 of the learning server 104 outputs a request to send learning data to the data server 105 (step S606). Seventh, upon receiving the request to send the learning data, the CPU 228 of the data server 105 sends the learning data, which is stored in the HDD 229 or the like at this point, to the learning server 104 (step S607).

Eighth, the CPU 220 of the learning server 104 creates a trained model, for example, the complete-recovery period prediction model 501 by carrying out a training process using the learning data received from the data server 105 (step S608). Ninth, after completing the training process, the CPU 220 of the learning server 104 sends the complete-recovery period prediction model 501 to the client terminal 102 (step S609). It should be noted that, in this process of sending the complete-recovery period prediction model 501 in the present embodiment, either the complete-recovery period prediction model 501 itself or trained coefficient parameters of the complete-recovery period prediction model 501 may be sent to the client terminal 102. The CPU 220 of the learning server 104 then stores the complete-recovery period prediction model 501 in the HDD 221.

Tenth, the CPU 212 of the client terminal 102 sends the complete-recovery period prediction model 501 received from the learning server 104 to the digital camera 101 (step S610). Eleventh, the CPU 201 of the digital camera 101 stores data on the complete-recovery period prediction model 501 received from the client terminal 102 in the storage unit 210 (step S611).

In the above-described flow of data from the step S601 to the step S611, the complete-recovery period prediction model 501 that has been trained is installed in the digital camera 101 and the learning server 104. Twelfth, a user uses the complete-recovery period prediction model 501 (step S612). Specifically, the user inputs affected-part image data shot by the digital camera 101 as unknown image data to the complete-recovery period prediction model 501 installed in the digital camera 101 or the learning server 104, so as to predict the number of days to a complete recovery of an affected part.

Figure 7A:
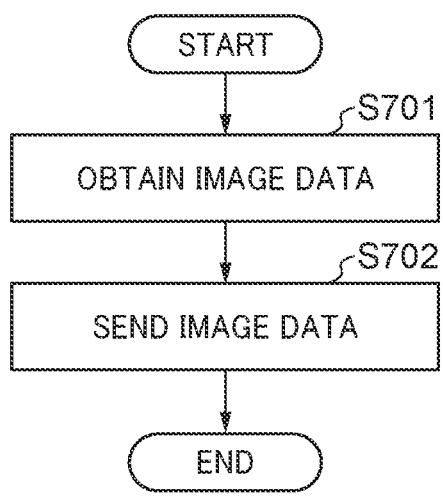
FIGS. 7A and 7B are flowcharts illustrating examples of processes that are carried out by a digital camera and a client terminal in a first collection control process.

Referring to FIGS. 7A, 7B, 8A to 8D, 9A, and 9B, a description will now be given of a first collection control process in which learning data for use in creating the complete-recovery period prediction model (training the complete-recovery period prediction model 501) is collected. The first collection control process is carried out by the digital camera 101, the client terminal 102, the learning server 104, and the data server 105. FIG. 7A is a flowchart illustrating an example of a process that is carried out by the digital camera 101 in the first collection control process. FIGS. 8A to 8D are views illustrating examples of the structure of image data for use in the first collection control process.

In S701, the CPU 201 of the digital camera 101 obtains image data to be used as learning data for creating the complete-recovery period prediction model 501. The image data is affected-part image data generated by the image pickup control unit 302 shooting an affected part. It should be noted that no data is recorded as metadata for the image data as illustrated in FIG. 8A. Next, in S702, the CPU 201 sends the obtained image data to the client terminal 102. Then, the process by the digital camera 101 is ended.

Figure 7B:
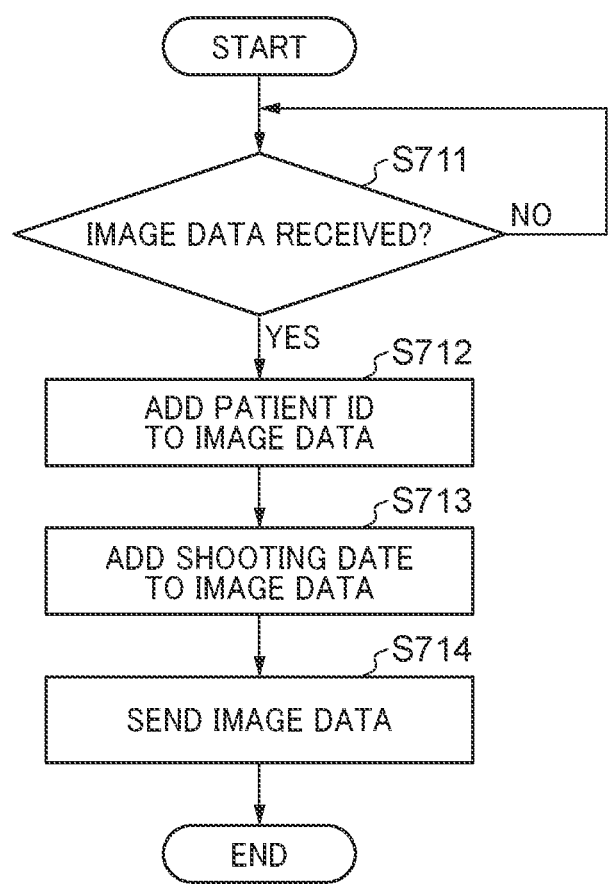

FIG. 7B is a flowchart illustrating an example of a process that is carried out by the client terminal 102 in the first collection control process. In S711, the CPU 212 of the client terminal 102 determines whether or not image data has been received from the digital camera 101. When the CPU 212 determines that image data has been received from the digital camera 101, the process proceeds to S712. When the CPU 212 determines that no image data has been received from the digital camera 101, the process returns to S711.

In S712, the CPU 212 adds an affected part ID to the received image data. As a result, the affected part ID is recorded as metadata for the image data received from the digital camera 101. The affected part ID is a unique ID for identifying an affected part of a patient. In the present embodiment, independent affected part IDs are assigned to respective patient's affected parts, and a user inputs one of the affected part IDs to the input unit 217 of the client terminal 102.

In S713, the CPU 212 adds a shooting date to the received image data. As a result, the date on which the image data was shot is recorded as metadata for the image data received from the digital camera 101. It should be noted that although in the description of the present embodiment, the client terminal 102 is configured to record the shooting date as the metadata for the image data, the present invention is not limited to this, but for example, the digital camera 101 may record the shooting date as the metadata for the image data. As a result of the processes in S712 and S713, the affected part ID and the shooting date are recorded as the metadata for the image data received from the digital camera 101 as illustrated in FIG. 8B.

In S714, the CPU 212 sends the image data in which the affected part ID and the shooting date are recorded as the metadata to the learning server 104. After that, the process by the client terminal 102 is ended.

Figure 9A:
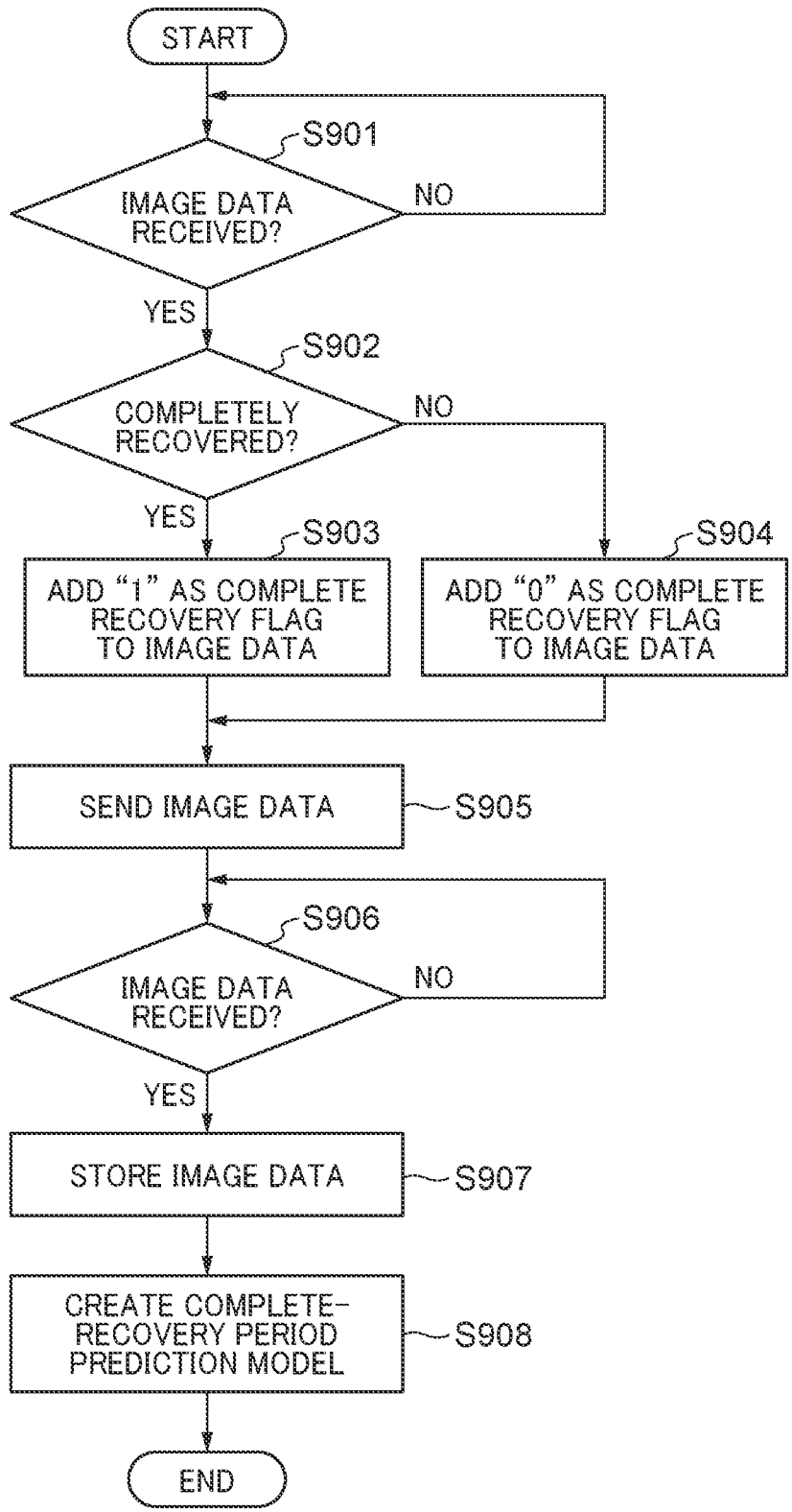
FIGS. 9A and 9B are flowcharts illustrating examples of processes that are carried out by a learning server and a data server in the first collection control process.

FIG. 9A is a flowchart illustrative an example of a process that is carried out by the learning server 104 in the first collection control process.

In S901, the CPU 220 of the learning server 104 determines whether or not image data has been received from the client terminal 102. When the CPU 220 determines that image data has been received from the client terminal 102, the process proceeds to S902. When the CPU 220 determines that no image data has been received from the client terminal 102, the process returns to S901.

In S902, based on the received image data, the CPU 220 determines whether or not the affected part has completely recovered. Specifically, the CPU 220 outputs the received image data to the prediction unit 316. The CPU 220 obtains from the prediction unit 316 the predicted presence/absence of injury/disease 405, which has been obtained by the prediction unit 316 inputting the affected-part image data 402, the injury/disease type data 403, and the auxiliary data 404 to the affected-part presence/absence prediction model 401. Based on the predicted presence/absence of injury/disease 405, the CPU 220 then determines whether or not the affected part has completely recovered. When the CPU 220 determines that the affected part has completely recovered, the process proceeds to S903. When the CPU 220 determines that the affected part has not completely recovered, the process returns to S904.

In S903, the CPU 220 adds "1" as a complete recovery flag, which indicates that the affected part has completely recovered, to the image data received from the client terminal 102. As a result, the complete recovery flag "1" is recorded as metadata for the image data received from the client terminal 102 as illustrated in FIG. 8C. After that, the process proceeds to S905.

In S904, the CPU 220 adds "0" as a complete recovery flag, which indicates that the affected part has not completely recovered, to the image data received from the client terminal 102. As a result, the complete recovery flag "0" is recorded as metadata for the image data received from the client terminal 102. After that, the process proceeds to S905.

In S905, the CPU 220 sends the image data in which the complete recovery flag is recorded as metadata to the data server 105. After that, the process proceeds to S906, which will be described later.

Figure 9B:
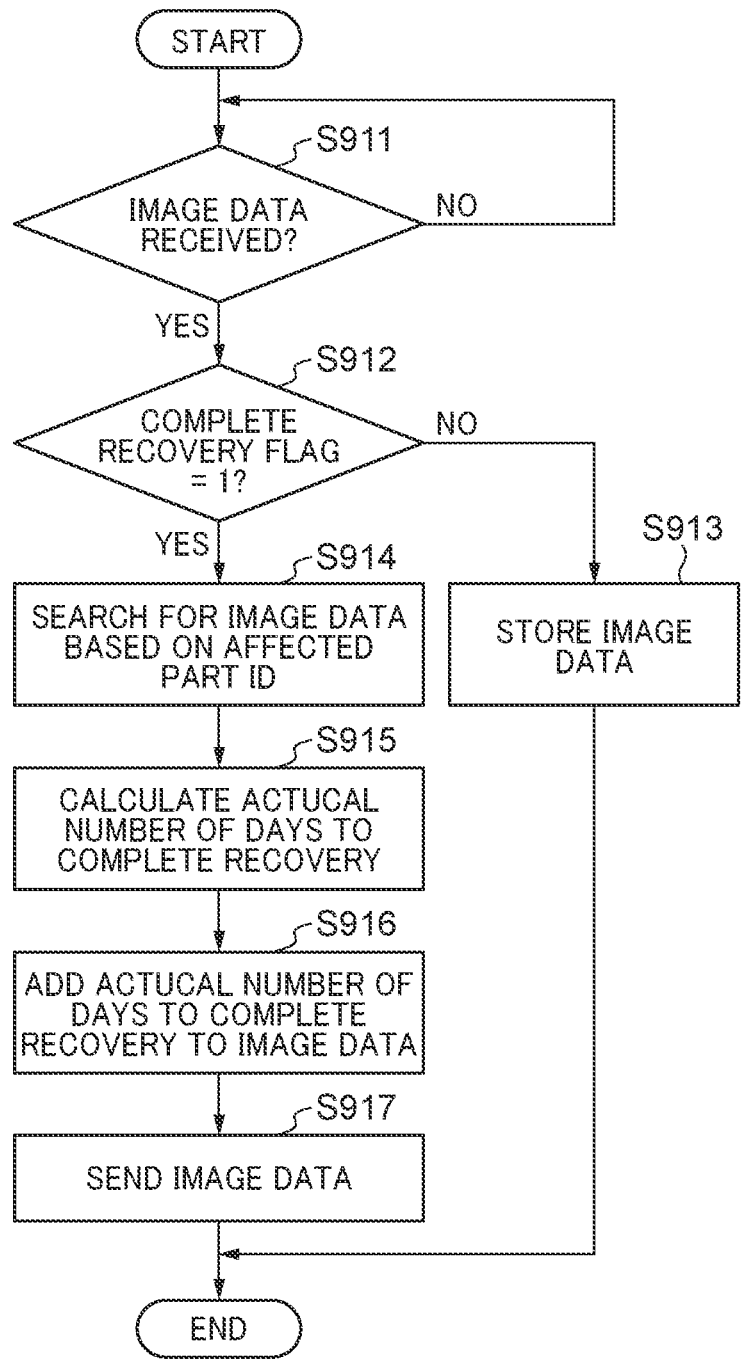

FIG. 9B is a flowchart illustrating an example of a process carried out by the data server 105 in the first collection control process.

In S911, the CPU 228 of the data server 105 determines whether or not image data has been received from the learning server 104. When the CPU 228 determines that image data has been received from the learning server 104, the process proceeds to S912. When the CPU 220 determines that no image data has been received from the learning server 104, the process returns to S911.

In S912, the CPU 228 determines whether or not the complete recovery flag "1" is recorded as metadata for the received image data. When the CPU 228 determines that the complete recovery flag "1" is not recorded as the metadata for the received image data, the process proceeds to S913. When the CPU 228 determines that the complete recovery flag "1" is recorded as the metadata for the received image data, the process proceeds to S914.

In S913, the CPU 228 stores the image data received from the learning server 104 in the HDD 229. After that, the process by the data server 105 is ended.

In S914, the CPU 228 searches for image data based on the affected part ID recorded as the metadata for the image data received from the learning server 104. Specifically, the CPU 228 searches a plurality of image data recorded in advance in the HDD 229 for image data, in which the same affected part ID as the affected part ID recorded as the metadata for the image data received from the learning server 104, and the complete recovery flag "0" are recorded. Then, in S915, by using the shooting date recorded as the metadata for the image data found in S914 as a reference, and regarding the shooting date recorded as the metadata date for the image data received from the learning server 104 as a date of complete recovery, the CPU 228 calculates the actual number of days to the complete recovery.

Then, in S916, the CPU 228 adds the actual number of days to the complete recovery to the image data received from the learning server 104. As a result, the actual number of days to the complete recovery is recorded as metadata for the image data received from the learning server 104 as illustrated in FIG. 8D. After that, in S917, the CPU 228 sends the image data, in which the actual number of days to the complete recovery is recorded as the metadata, to the learning server 104. Then, the process by the data server 105 is ended.

Referring again to FIG. 9A, the CPU 220 of the learning server 104 determines in S906 whether or not image data has been received from the data server 105. When the CPU 220 determines that image data has been received from the data server 105, the process proceeds to S907. When the CPU 220 determines that no image data has been received from the data server 105, the process returns to S906.

In S907, the CPU 220 stores the image data received from the data server 105 in the HDD 221. Then, in S908, the CPU 220 creates the complete-recovery period prediction model 501 using the received image data. Specifically, the CPU 220 outputs the received image data to the learning unit 314, and the learning unit 314 inputs the obtained image data as training data to a learning model and trains the learning model by machine learning. The process creates, as described above, the complete-recovery period prediction model 501 that outputs the predicted recovery period of injury/disease 505 when the affected-part image data 502, the injury/disease type data 503, and the auxiliary data 504 are input as unknown image data. After that, the process by the learning server 104 is ended.

According to the embodiment described above, from among image data set stored in advance in the HDD 229 (storage device), image data accompanied with the same affected part ID as that of the affected-part image data is identified, and the actual number of days to a complete recovery is then calculated based on a shooting date of the identified image data and a shooting date of the affected-part image data. The affected-part image data accompanied with the actual number of days to the complete recovery is used, as training data, in other words, input to a learning model, so as to create the complete-recovery period prediction model 501. As a result, data of affected parts having completely recovered to be used as training data can be easily collected.

Moreover, in the embodiment described above, whether or not an affected part has completely recovered is determined based on the predicted presence/absence of injury/disease 405 obtained by inputting affected-part image data to the affected-part presence/absence prediction model 401. This reduces the time and effort required for a doctor to determine whether an affected part has completely recovered in a process of collecting data of affected parts having completely recovered to be used as training data.

Although the present invention has been described by way of the embodiment, the present invention should not be limited to the embodiment described above. For example, the complete-recovery period prediction model 501 may be retrained by carrying out a second collection control process.

The second collection control process is similar to the first collection control process described above and differs from the first collection control process described above in terms of a process carried out by the learning server 104 and the process carried out by the data server 105. Only features different from those of the first collection control process described above will be described below. It is assumed that in the second collection control process, the complete-recovery period prediction model 501 has already been created by carrying out the first collection control process described above, and the prediction unit 316 of the learning server 104 is capable of predicting the number of days to a complete recovery of an affected part using the complete-recovery period prediction model 501.

FIGS. 10A to 10C are views illustrating examples of the structure of image data for use in the second collection control process. In the second collection control process, first, the above-described process by the digital camera 101 in FIG. 7A and the above-described process by the client terminal 102 in FIG. 7B are carried out. As a result, image data in which an affected part ID and a shooting date are recorded as metadata is sent to the learning server 104 as illustrated in FIG. 10A.

Figure 11:
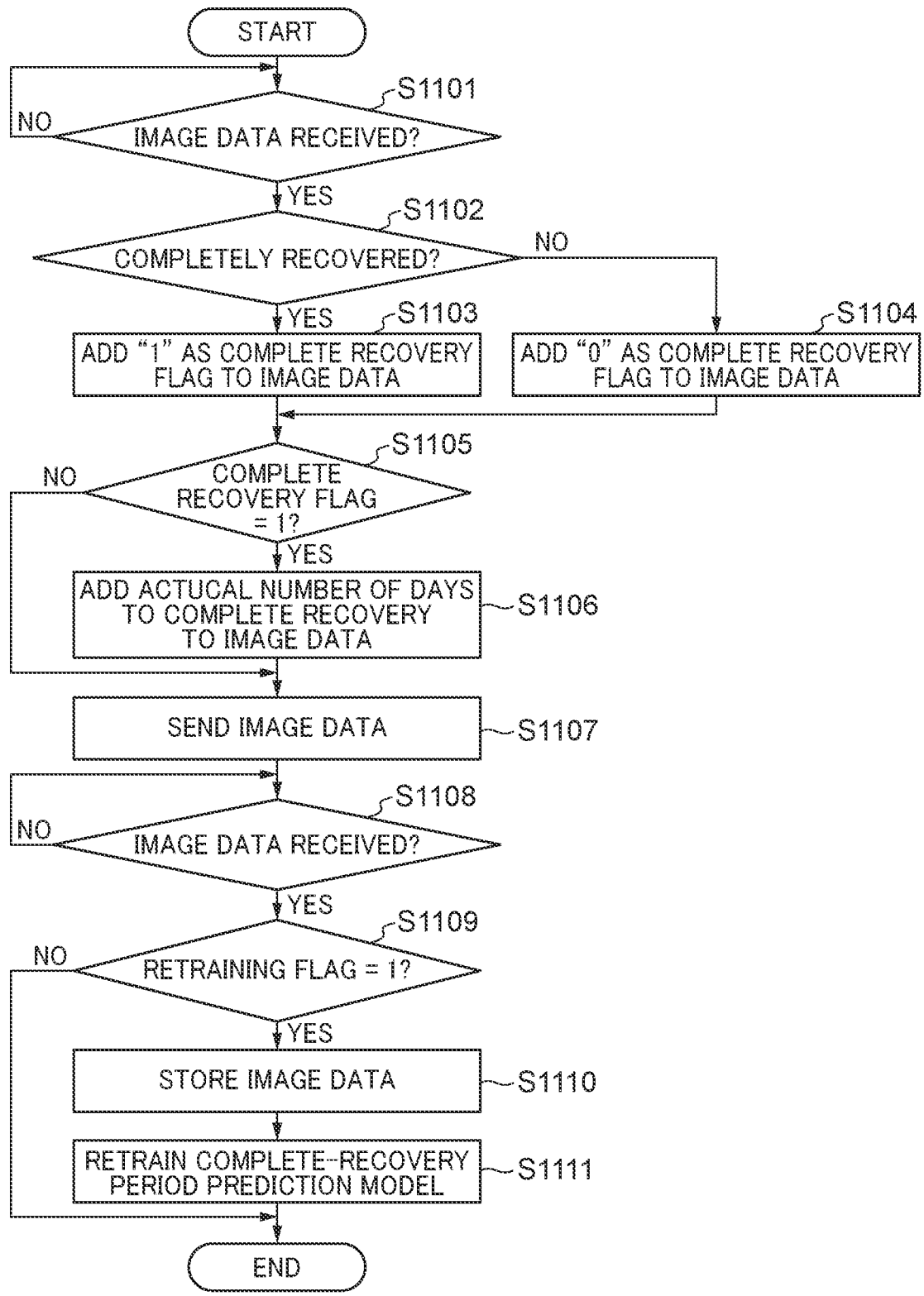
FIG. 11 is a flowchart illustrating an example of a process that is carried out by the learning server in the second collection control process.

FIG. 11 is a flowchart illustrating an example of a process that is carried out by the learning server 104 in the second collection control process. Referring to FIG. 11, the CPU 220 of the learning server 104 carries out processes in S1101 to S1104 which are the same as the processes in S901 to S904 described above. Next, in S1105, the CPU 220 determines whether or not "1" is recorded as the complete recovery flag in metadata for the image data. When the CPU 220 determines that "1" is recorded as the recovery flag in the metadata for the image data, the process proceeds to S1106. When the CPU 220 determines that "1" is not recorded as the complete recovery flag in the metadata for the image data, the process proceeds to S1107.

In S1106, the CPU 220 adds the predicted number days to the complete recovery to the image data. Specifically, the CPU 220 loads the image data into the prediction unit 316. The prediction unit 316 inputs the image data, injury/disease type data 503, and auxiliary data 504 as unknown data to the complete-recovery period prediction model 501 and outputs the predicted recovery period of injury/disease 505. As illustrated in FIG. 10B, the CPU 220 records the predicted recovery period of injury/disease 505, which is the predicted number of days to the complete recovery, in metadata for the image data.

In S1107, the CPU 220 sends the image data in which various pieces of data are recorded as the metadata to the data server 105. For example, when the CPU 220 determines in S1105 that "1" is recorded as the complete recovery flag in the metadata for the image data, the image data in which the predicted number days to the complete recovery is recorded as the metadata is sent to the data server 105. After that, the process proceeds to S1108, which will be described later.

Figure 12:
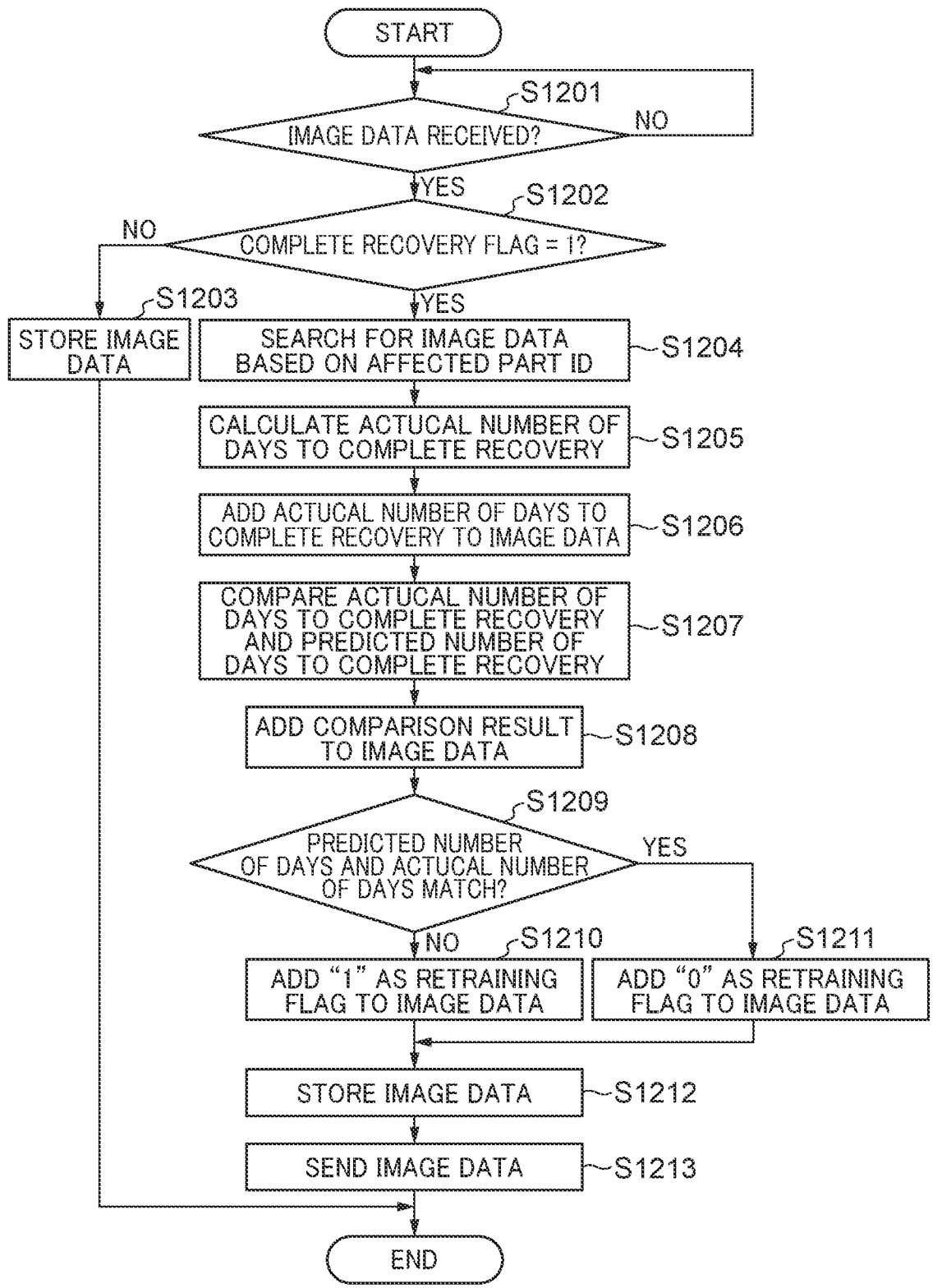
FIG. 12 is a flowchart illustrating an example of a process that is carried out by the data server in the second collection control process.

FIG. 12 is a flowchart illustrating an example of a process that is carried out by the data server 105 in the second collection control process. Referring to FIG. 12, the CPU 228 of the data server 105 carries out processes in S1201 and S1202 which are the same as the processes in S911 and S912 described above. When the CPU 228 determines in S1202 that "1" is not recorded as the complete recovery flag in metadata of received image data, the process proceeds to S1203, which is the same as S913 described above. Then, the process by the data server 105 is ended.

When the CPU 228 determines in S1202 that "1" is recorded as the complete recovery flag in the metadata for the image data, the process proceeds to S1204 to S1206, which are the same as S914 to S916 described above. Then, the CPU 228 compares the predicted number of days to the complete recovery recorded in the metadata for the received image data with the actual number of days to the complete recovery calculated in S1206.

Then, in S1208, the CPU 228 adds a result of the comparison in S1207 to the image data. The result of the comparison is thus recorded in the metadata for the received image data as illustrated in FIG. 10C. For example, the number days calculated by subtracting the actual number of days to the complete recovery from the predicted number of days to the complete recovery is recorded as the result of the comparison in the metadata for the received image data. It should be noted that data recorded in the metadata of the received image data in S1208 is not limited to the number of days calculated by subtracting the actual number of days to the complete recovery from the predicted number of days to the complete recovery but may be data indicating whether or not the predicted number of days to the complete recovery matches the actual number of days to the complete recovery.

Then, in S1209, based on the result of the comparison, the CPU 228 determines whether or not the predicted number of days to the complete recovery matches the actual number of days to the complete recovery. When the CPU 228 determines that the predicted number of days to the complete recovery does not match the actual number of days to the complete recovery, the process proceeds to S1210. When the CPU 228 determines that the predicted number of days to the complete recovery matches the actual number of days to the complete recovery, the process proceeds to S1211.

In S1210, the CPU 228 adds a retraining flag, which indicates that retraining is to be performed, to the image data. For example. "1" is recorded as the retraining flag in metadata for the image data as illustrated in FIG. 10C. The process then proceeds to S1212. In S1211, the CPU 228 adds "0" as a retraining flag, which indicates that retraining is not to be performed, to the image data. As a result, "0" is recorded as the retraining flag in metadata for the image data. Then, the process proceeds to S1212.

In S1212, the CPU 228 stores the image data in which various pieces of data are recorded as the metadata to the HDD 220. Then, in S1213, the CPU 228 sends the image data to the learning server 104. After that, the process by the data server 105 is ended.

Referring again to FIG. 11, in S1108, the CPU 228 determines whether or not image data has been received from the data server 105. When the CPU 220 determines that image data has been received from the data server 105, the process proceeds to S1109. When the CPU 220 determines that no image data has been received from the data server 105, the process returns to S1108.

In S1109, the CPU 220 determines whether or not "1" is recorded as the retraining flag in metadata for the image data received from the data server 105. When the CPU 220 determines that "1" is recorded as the retraining flag in the metadata for the image data received from the data server 105, the process proceeds to S1110. When the CPU 220 determines that "1" is not recorded as the retraining flag in the metadata for the image data received from the data server 105, the process by the learning server 104 is ended.

In S1110, the CPU 220 stores the image data received from the data server 105 in the HDD 221. Then, in S1111, the CPU 220 uses the image data received from the data server 105 to retrain the complete-recovery period prediction model 501. Specifically, the CPU 220 loads the image data into the learning unit 314. The learning unit 314 uses the obtained image data as training data to retrain the complete-recovery period prediction model 501. As a result, the complete-recovery period prediction model 501 is updated. After that, the process by the learning server 104 is ended.

In the embodiment described above, when the predicted number of days to the complete recovery does not match the actual number of days to the complete recovery, affected-part image data accompanied with the actual number of days to the complete recovery is input as training data to the complete-recovery period prediction model 501 to retrain the complete-recovery period prediction model 501. As a result, training data for retraining the complete-recovery period prediction model 501 can be easily collected.

It should be noted that in the embodiment described above, for example, individual difference information may be added to the affected-part image data to be used as the training data.

Here, the number of days to a complete recovery of an affected part vary with patients. Moreover, in a case where a doctor makes a final judgement as to whether or not an affected part has completely recovered while referring to a prediction result output from the affected-part presence/absence prediction model 401, the judged number of days to a complete recovery of an affected part vary with doctors because criteria for the judgement vary with doctors. Thus, the number of days to the complete recovery vary among individuals, and hence from the viewpoint of improving prediction accuracy, it is preferred that complete-recovery period prediction model 501 learns individual difference information on an affected part.

Accordingly, in the present embodiment, a third collection control process is carried out to add individual difference information on an affected part to affected-part image data to be used as training data.

The third collection control process is similar to the first collection control process described above and differs from the first collection control process described above in terms of a process carried out by the client terminal 102. Only features different from those of the first collection control process described above will be described below.

In the third collection control process, first, the digital camera 101 carries out the process described above with reference to FIG. 7A. Thus, image data generated by the image pickup control unit 302 shooting an affected part is sent to the client terminal 102. It should be noted that no data is recorded as metadata for the image data.

FIG. 13 is a flowchart illustrating an example of a process that is carried out by the client terminal 102 in the third collection control process. FIGS. 14A and 14B are views illustrating examples of the structure of image data for use in the third collection control process. Referring to FIG. 13, the CPU 212 of the client terminal 102 carries out processes in S1301 and S1302, which are the same as the processes in S1001 and S1002 described above. Next, in S1303, the CPU 212 adds a patient ID to image data received from the digital camera 101. As a result, the patient ID is recorded as metadata for the image data received from the digital camera 101. The patient ID is a unique ID for identifying a patient. In the present embodiment, independent patient IDs are assigned to respective patients. A user may input one of the patient IDs to the input unit 217 of the client terminal 102. It should be noted that the patient ID should not always be obtained in this manner, but for example, the patient ID may be obtained by reading a barcode or reading a near field wireless IC.

Then, in S1304, the CPU 212 adds a doctor ID to the image data received from the digital camera 101. As a result, the doctor ID is recorded as metadata for the image data received from the digital camera 101. The doctor ID is a unique ID for identifying a doctor. In the present embodiment, independent doctor IDs are assigned to respective doctors. As with the patient ID, a user may input one of the doctor IDs to the input unit 217 of the client terminal 102. It should be noted that the doctor ID should not always be obtained in this manner, but for example, the doctor ID may be obtained by reading a barcode or reading a near field wireless IC. After that, the CPU 212 carries out processes in S1305 and S1306, which are the same as the processes in S1003 and S1004 described above. As a result, the image data in which, for example, an affected part ID, a patient ID, a doctor ID, and a shooting date are recorded as metadata as illustrated in FIG. 14A is sent to the learning server 104. Then, the process by the client terminal 102 is ended. Thus, based on the image data sent to the learning server 104, the process by the learning server 104 in FIG. 9A and the process by the data server 105 in FIG. 9B are carried out, and the image data in FIG. 14B is input to the learning model to perform machine learning. As a result, the complete-recovery period prediction model 501 is created. As metadata for image data in FIG. 14B, individual difference information on an affected part i.e., a patient ID and a doctor ID are recorded in addition to an affected part ID, a shooting date, and the number of days to the complete recovery.

In the embodiment described above, individual difference information on an affected part as well as the actual number of days to the complete recovery is added to affected-part image data to be input as training data to the learning model. As a result, training data for learning individual differences in the number days to the complete recovery of an affected part can be easily collected.

Moreover, in the embodiment described above, individual difference information on an affected part includes a patient ID. As a result, training data for learning individual differences in the number days to the complete recovery of an affected part resulting from differences of patients can be easily collected.

Furthermore, in the embodiment described above, individual difference information on an affected part includes a doctor ID. As a result, training data for learning individual differences in the number of days to the complete recovery of an affected part resulting from differences of doctors in charge can be easily collected.

It should be noted that although in the embodiment described above, the learning system 100 includes the digital camera 101, the client terminal 102, the learning server 104, and the data server 105, the present invention is not limited to this arrangement. For example, the learning system 100 may include any arrangement as long as it includes at least the learning server 104 and the data server 105.

Moreover, the learning server 104 and the data server 105 should not always be configured as separate units but may be configured as a single unit.

Other Embodiments

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing remit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

This application claims the benefit of Japanese Patent Application No. 2021-194558 filed on Nov. 30, 2021 which is hereby incorporated by reference wherein in its entirety.

What is claimed is:

1. A learning system comprising:
a storage device; and
at least one processor and/or at least one circuit configured to perform operations of:
based on affected-part image data generated by shooting an affected part, making a determination whether or not the affected part has completely recovered;
in a case where it is determined that the affected part has completely recovered, identifying image data accompanied with a same affected part ID as an affected part ID of the affected-part image data from among a plurality of image data stored in advance in the storage device, and calculating an actual number of days to a complete recovery of the affected part, based on a shooting date of the identified image data and a shooting date of the affected-part image data;
adding the actual number of days to the complete recovery to the affected-part image data; and
using, as training data, the affected-part image data accompanied with the actual number of days to the complete recovery to create a trained model that predicts a number of days to a complete recovery of the affected part;
in case where it is determined that the affected part has completely recovered, making a comparison between a predicted number of days to the complete recovery, which is obtained by inputting the affected-part image data as unknown image data to the trained model, and the actual number of days to the complete recovery; and
in a case where the comparison results in that the predicted number of days to the complete recovery does not match the actual number of days to the complete recovery, retraining the trained model by inputting, as training data, the affected-part image data accompanied with the actual number of days to the complete recovery to the trained model.

2. The learning system according to claim 1, wherein to the affected-part image data to be used as the training data, individual difference information on the affected part is added along with the actual number of days to the complete recovery.

3. The learning system according to claim 2, wherein the individual difference information on the affected part includes a patient ID for identifying a patient.

4. The learning system according to claim 2, wherein the individual difference information on the affected part includes a doctor ID for identifying a doctor.

5. The learning system according to claim 1, wherein the at least one processor and/or the at least one circuit is configured to perform further operations of: in the determination, determining whether or not the affected part has completely recovered based on a prediction result obtained by inputting the affected-part image data to another trained model that predicts presence or absence of the affected part.

6. A control method for a learning system including a storage device, the control method comprising:
- based on affected-part image data generated by shooting an affected part, making a determination whether or not the affected part has completely recovered;
- in a case where it is determined that the affected part has completely recovered, identifying image data accompanied with a same affected-part ID as an affected part ID of the affected-part image data from among a plurality of image data stored in advance in the storage device, and calculating an actual number of days to a complete recovery of the affected part, based on a shooting date of the identified image data and a shooting date of the affected-part image data;
- adding the actual number of days to the complete recovery to the affected-part image data; and
- using, as training data, the affected-part image data accompanied with the actual number of days to the complete recovery to create a trained model that predicts a number of days to a complete recovery of the affected part;
- in case where it is determined that the affected part has completely recovered, making a comparison between a predicted number of days to the complete recovery, which is obtained by inputting the affected-part image data as unknown image data to the trained model, and the actual number of days to the complete recovery; and
- in a case where the comparison results in that the predicted number of days to the complete recovery does not match the actual number of days to the complete recovery, retraining the trained model by inputting, as training data, the affected-part image data accompanied with the actual number of days to the complete recovery to the trained model.

7. A non-transitory computer-readable storage medium storing a program for causing a computer to execute a control method for a learning system including a storage device, the control method comprising:
- based on affected-part image data generated by shooting an affected part, making a determination whether or not the affected part has completely recovered;
- in a case where it is determined that the affected part has completely recovered, identifying image data accompanied with a same affected-part ID as an affected part ID of the affected-part image data from among a plurality of image data stored in advance in the storage device, and calculating an actual number of days to a complete recovery of the affected part, based on a shooting date of the identified image data and a shooting date of the affected-part image data;
- adding the actual number of days to the complete recovery to the affected-part image data; and
- using, as training data, the affected-part image data accompanied with the actual number of days to the complete recovery to create a trained model that predicts a number of days to a complete recovery of the affected part;
- in case where it is determined that the affected part has completely recovered, making a comparison between a predicted number of days to the complete recovery, which is obtained by inputting the affected-part image data as unknown image data to the trained model, and the actual number of days to the complete recovery; and
- in a case where the comparison results in that the predicted number of days to the complete recovery does not match the actual number of days to the complete recovery, retraining the trained model by inputting, as training data, the affected-part image data accompanied with the actual number of days to the complete recovery to the trained model.

* * * * *